(12) United States Patent
Su et al.

(10) Patent No.: US 10,543,191 B2
(45) Date of Patent: Jan. 28, 2020

(54) USE OF BUTYLIDENEPHTHALIDE (BDPH), METHOD OF USING THE SAME, AND METHOD FOR PREPARING PHARMACEUTICAL COMPOSITION CONTAINING THE SAME

(71) Applicant: EJIA BIOTECHNOLOGY CO., LTD, Taichung (TW)

(72) Inventors: Hong-Lin Su, Taichung (TW); Chia-Yu Chang, Yunlin County (TW); Shiaw-Min Hwang, Hsinchu (TW); Huai-En Lu, Kaohsiung (TW); Horng-Jyh Harn, Taipei (TW); Shinn-Zong Lin, Taichung (TW); Ping-Shan Lai, Taichung (TW)

(73) Assignee: Ejia Biotechnology Co., Ltd., Taichung (TW)

( * ) Notice: Subject to any disclaimer, the term of this patent is extended or adjusted under 35 U.S.C. 154(b) by 0 days.

(21) Appl. No.: 15/629,616

(22) Filed: Jun. 21, 2017

(65) Prior Publication Data

US 2018/0207127 A1    Jul. 26, 2018

Related U.S. Application Data

(63) Continuation of application No. 15/329,051, filed on Jan. 25, 2017.

(51) Int. Cl.
*A61K 31/365* (2006.01)
*A61Q 7/00* (2006.01)
(Continued)

(52) U.S. Cl.
CPC .......... *A61K 31/365* (2013.01); *A61K 8/4973* (2013.01); *A61K 36/23* (2013.01);
(Continued)

(58) Field of Classification Search
CPC ................. A61K 31/365; A61Q 7/06
(Continued)

(56) References Cited

U.S. PATENT DOCUMENTS

2006/0235370 A1 * 10/2006 Oblong ................ A61B 18/203
606/9

FOREIGN PATENT DOCUMENTS

JP         3-135907 A  *  6/1991  ........... A61K 31/185

OTHER PUBLICATIONS

Machine Translation of JP 3-135907A, Jun. 10, 1991, pp. 1-4.*

* cited by examiner

*Primary Examiner* — Craig D Ricci
*Assistant Examiner* — Janet L. Coppins
(74) *Attorney, Agent, or Firm* — Muncy, Geissler, Olds & Lowe, P.C.

(57) ABSTRACT

The present invention discloses use of butylidenephthalide (Bdph), a method of using the same, and a method for preparing a pharmaceutical composition containing the same. Because Bdph has the capability of promoting the hair growth and reducing the β-amyloid protein (Aβ) level in nerve cells, the efficacy of improving the health and appearance of a subject can be achieved by administrating an effective amount of Bdph to the subject. Specifically, the Bdph has the efficacy of preventing or treating neurodegenerative diseases such as Alzheimer's disease caused by excessive build up of Aβ in the cells, and as an active ingredient in a topical composition, the Bdph is effective in promoting the hair growth at the site where the Bdph is administered. Furthermore, the method for preparing a pharmaceutical composition containing Bdph comprises preparing the pharmaceutical composition through an organic synthesis reaction, wherein the Bdph is coated with a
(Continued)

polymeric material such as F127 by covalent bonding of the polymeric material with the Bdph, thereby achieving the effect of reducing the cytotoxicity of the pharmaceutical composition for an organism.

8 Claims, 6 Drawing Sheets

(51) Int. Cl.
*A61K 8/49* (2006.01)
*A61K 36/28* (2006.01)
*A61K 36/23* (2006.01)

(52) U.S. Cl.
CPC ................ *A61K 36/28* (2013.01); *A61Q 7/00* (2013.01); *A61K 2800/74* (2013.01)

(58) Field of Classification Search
USPC .......................................................... 514/470
See application file for complete search history.

USE OF BUTYLIDENEPHTHALIDE (BDPH), METHOD OF USING THE SAME, AND METHOD FOR PREPARING PHARMACEUTICAL COMPOSITION CONTAINING THE SAME

BACKGROUND OF THE INVENTION

1. Field of the Invention

The present invention relates to use of a compound, particularly use of butylidenephthalide (Bdph), a method of using the same, and a method for preparing a pharmaceutical composition containing the same.

2. Description of the Related Art

Due to the increased survival time of modern people, more and more people face a variety of diseases affecting the health and also the problem of aging appearance with increased age and multiplied life stress. Specifically, Alzheimer's disease is the most prevalent neurodegenerative disease in the whole world, and the main pathological features comprise excessive deposition of β-amyloid protein (Aβ) forming the Aβ plaque in the brain (Glenner and Wong 1984; and Masters, C. L. et al., 1985) and intracellular neurofibrillary tangles (NFT) (Grundke-lqbal, I. et al., 1986; and Goedert, M. et al., 1988). The Aβ plaque is produced from amyloid protein precursor (APP) after cleavage by the β-site amyloid precursor protein cleaving enzyme (BACE) (Hussain, I. et al., 1999; and Vassar, R. et al., 1999) and the γ-secretase (Wolfe, M. S. et al., 1999; and Yu, G. et al., 2000), and consists essentially of Aβ40 and Aβ42 (Jarrett, J. T. et al., 1993). Large intra- and extracelluar accumulation of Aβ is a main cause of neuronal cell death.

The pathogenesis of Down's syndrome is uneven split of the 21th pair of chromosomes during meiosis, causing 1 additional chromosome to exist in the cell. The gene encoding the APP is located on the chromosome 21 (Rumble, B. et al., 1989; and Selkoe, D. J., 1996). It is generally accepted that the over-expression of APP leads to a symptom of early cognitive impairment in the patients with Down's syndrome (Burger, P. C. and F. S. Vogel, 1973). At present, many studies show that the Aβ plaque is found in the brain of patients with Down's syndrome (Masters, C. L. et al., 1985; Beyreuther, K. et al., 1992; Gyure, K. A. et al., 2001; and Mori, C. et al., 2002). Other studies show that the nerve cells produced by induced pluripotent stem cells (iPSCs) derived from patients with Down's syndrome can be used to reproduce the typical pathological features of Alzheimer's disease, for example, accumulation of Aβ42 and Aβ40, highly phosphorylated Tau protein, and others. Therefore, an iPSC differentiation system from patients with Down's syndrome can be used as a platform for screening drugs for treating or preventing Aβ-related neurodegenerative diseases.

The drugs for treating Alzheimer's disease currently available in clinic comprise cholinesterase inhibitors (Birks, J., 2006) and NMDA receptor antagonists (McShane, R. et al., 2006), both of which are suitable for improving the cognitive function of patients with Alzheimer's disease. However, the diseases derived from Alzheimer's disease, such as depression, insomnia, and so on, need to be treated with other suitable medications (Tariot, P. N. et al., 2004; Feldman, H. et al., 2006; and Howard, R. et al., 2012). Moreover, the two types of drugs can only ameliorate the symptoms, and cannot achieve the efficacy of curing Alzheimer's disease (Farlow, M. R. et al., 2010). Besides, in many studies, drugs for treating Alzheimer's disease are designed for reducing Aβ accumulation in the brain (Hong-Qi, Y. et al., 2012), and comprise specifically BACE inhibitors, for example, MK-8931 and ACI-91 (Mullard A., 2012), γ-secretase inhibitors, for example, LY450139 (Siemers, E. et al., 2005) and BMS-708163 (Tong, G. et al., 2012), or antibodies against Aβ by way of immunization.

Furthermore, although problems such as local alopecia, hair loss, or hypotrichosis do not adversely affect the health of an individual, they undeniably affect the appearance of the individual. Research suggests that those with hypotrichosis are prone to poor mood and unable to socialize, and may suffer from psychological problems such as social anxiety, insufficient self-confidence, and self-identity. Therefore, hypotrichosis or hair loss has become a problem received more and more attention at present.

In addition to the way to retarding the hair loss by changing the hair washing and dietary habits, there are many products for ameliorating the hair loss or promoting the hair growth available at present. The products are mainly divided into two classes, one class is vasodilators, and the other is prostaglandin-related derivatives. Further, among the vasodilators, the most well-known is "Regoine" (trade name minoxidil; Messenger A. G. et al., 2004), which is mainly composed of 2,4-diamino-6-piperidinopyrimidine 3-oxide. However, Regoine does not perform well for the hypotrichosis in each case, and the effect persists only when the product is used. Once the product is withdrawn, the newly grown hair will fall off again. It is reported that the prostaglandins F2α and E2 can be used to promote the eyelash and hair growth (Woodward, D. F. et al., 2013), but cause the side effects such as redness, irritation, pigmentation and the like to the user. Moreover, once the product is withdrawn, the newly grown hair will fall off too.

Butylidenephthalide (Bdph) is present in natural plants, for example, plants of the Apiaceae and Asteraceae family, and may be obtained by extraction with acetone and chloroform. Previous studies show that Bdph is useful in the treatment of spasm (Ko, W. C. et al., 1980) and inhibition of platelet aggregation (Teng, C. M. et al., 1987), and can suppress the cell growth and promote the cancer cell death. For example, the efficacy of inhibiting the tumor growth can be achieved by inhibiting the telomerase (Huang, M. H. et al., 2014; and Tsai, N. M. et al., 2006), and the efficacy of inhibiting the inflammatory response can be achieved by inhibiting NF-κB (Fu, R. H. et al., 2011). Furthermore, recent studies also show that Bdph can maintain the growth of embryonic stem cells and promote the formation of iPSCs by activating the Jak2/stat3 signaling pathway (Liu, S. P. et al., 2012).

The Wnt protein is a highly conserved secretary molecule, and an important factor for regulating the embryonic development and the stem cell maintenance. Wnt forms a ternary structure by binding to its receptor Frizzled (Frz) and LDL receptor-related proteins on the cell membrane, and acts on the Dishevelled (Dsh) in the cells. Dsh binds to GSK-3β, the adenomatous polyposis coli protein and the Axin protein to inhibit the activity of GSK-3β, thereby inhibiting the β-catenin phosphorylation and the pathway of β-catenin degradation via ubiquitination. Activation of the Wnt signaling can induce the intracellular accumulation of β-catenin. After entering the nucleus, the β-catenin can activate other particular transcription factors, such as T-cell factors, lymphoid enhancer factors and Siamois, etc., to regulate the growth of cells and the development of an individual. Over or under activation of the Wnt signaling in the cells can cause damage to the organism, cause defects in early embryonic development, or cause tumor formation or dysfunction in late adulthood (Fodde, R. et al., 2007).

At present, many researches confirm that the efficacy of promoting the hair growth can be achieved with activation of Wnt by stimulating the replication of epidermal stem cells (Lim, X. et al., 2013). The epidermal stem cells are mostly present in hair follicle bulges, which are label-retaining cells, usually in a dormant state, and activated only when the epidermis is damaged or the tissue needs to be freshed. The Wnt/β-catenin pathway is an imoportant component in the maintenance of self-replication of epidermal stem cells. Activation of the Wnt signaling allows the dormant epidermal stem cells to enter a cell cycle for cell replication and differentiation into mature hair cells (Thompson, C. C. et al., 2006). Wnt7a expression can increase the number of hair follicles reproduced. Similarly, the β-catenin level in the nucleus can be increased by stabilizing the β-catenin against degradation via ubiquitination, thereby promoting the formation of new hair follicles (Gat, U. et al., 1998). On the contrary, inhibition of the Wnt signaling can prevent the formation of hair follicles caused by wounds (Ito, M. et al., 2007).

It can be known from the foregoing description that the prior art cannot provide an effective composition having no side effects for treating or preventing neurodegenerative diseases such as Alzheimer's disease; as well as for improving alopecia or promoting the hair growth. Therefore, it is the most important research topic at present to develop a novel composition effective in improvement or treatment of the above-mentioned symptoms.

SUMMARY OF THE INVENTION

Accordingly, the present invention discloses use of butylidenephthalide (Bdph) and/or an analog thereof as an active ingredient in a topical composition for promoting the hair growth, or as an active ingredient in a pharmaceutical composition for treating or preventing neurodegenerative diseases.

A main objective of the present invention is to provide a topical composition for promoting the hair growth, with which the efficacy of effectively promoting the hair growth can be achieved while the adverse effect for human is reduced.

To achieve the above objective, the present invention discloses use of Bdph and/or an analog thereof, in which the Bdph, or an analog or a combination thereof is used in the preparation of a topical composition for promoting the hair growth, and the Bdph is capable of activating Wnt signaling.

Preferably, the Bdph is extracted from natural plants, for example, plants of the Apiaceae and Asteraceae family, where the extraction technology used is well known to those skilled in the art.

Preferably, the Bdph or the analog thereof is prepared through a chemical synthesis technology, where the chemical synthesis technology used is a chemical synthesis method well known to those skilled in the art.

Another objective of the present invention is to provide a method for promoting the hair growth, comprising: applying a topical composition for promoting the hair growth to the skin of a subject, where the topical composition comprises an effective amount of Bdph or an analog or a combination thereof, and a pharmaceutically or cosmetically acceptable carrier.

Preferably, the skin is a region having hair follicles.

Preferably, the topical composition for promoting the hair growth is directly applied onto the skin of the subject.

Preferably, the topical composition for promoting the hair growth is sprayed onto the skin of the subject.

Preferably, the concentration of Bdph is from 1 μM to 1 mM.

A further objective of the present invention is to provide use of Bdph and/or an analog thereof in the prevention or treatment of neurodegenerative diseases, such as Alzheimer's disease.

To achieve the above objectives, an embodiment of the present invention discloses a method for treating neurodegenerative diseases, comprising administrating a pharmaceutical composition comprising an effective amount of Bdph, or an analog or a combination thereof to a subject.

Preferably, the neurodegenerative disease is a sign with excessive build up of Aβ in the brain.

Preferably, the neurodegenerative disease is Alzheimer's disease.

Preferably, the Bdph is extracted from natural plants, for example, plants of the Apiaceae and Asteraceae family, where the extraction technology used is well known to those skilled in the art.

Preferably, the Bdph is prepared through a chemical synthesis technology, where the chemical synthesis technology used is a chemical synthesis method well known to those skilled in the art Another objective of the present invention is to provide a method for preparing a pharmaceutical composition, by which the cytotoxicity of the active ingredient in the pharmaceutical composition is reduced, thereby achieving the effect of increasing the safety and reducing the side effects of the pharmaceutical composition.

To achieve the objective of the present invention, the method for preparing a pharmaceutical composition disclosed in the present invention comprises mixing Bdph with a polymeric material at a weight ratio of 1:1-1:2, adding a polar organic solvent and water, coating the Bdph with the polymeric material in the aqueous phase by means of adsorption through intermolecular attraction, and then removing the polar organic solvent.

Preferably, the polar organic solvent is a heterocyclic ether compound.

Preferably, the polar organic solvent is tetrahydrofuran.

Preferably, the polymeric material is the F127 polymer.

Preferably, the polar organic solvent is removed by heating.

DETAILED DESCRIPTION OF THE PREFERRED EMBODIMENTS

Figure 1:
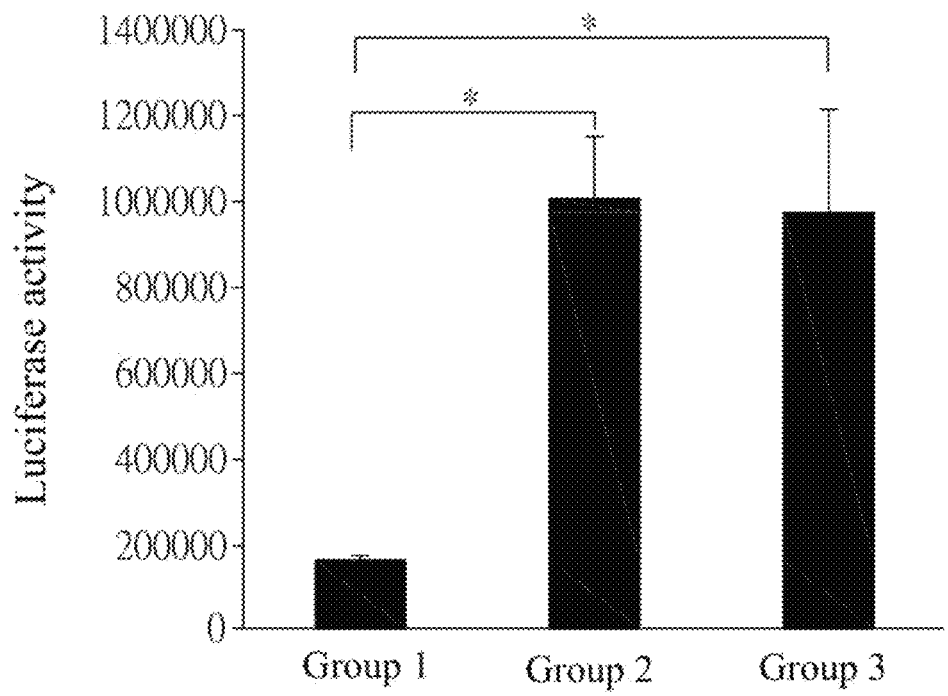
FIG. 1 shows statistical analysis results for luciferase expression detected in each group of cells after the groups of cells transfected with Top-flash plasmid DNA are cultured under various conditions.

The present invention discloses use of butylidenephthalide (Bdph), a method of using the same, and a method for preparing a pharmaceutical composition containing the same. Because Bdph has the capability of promoting the hair growth and reducing the β-amyloid protein (Aβ) level in nerve cells, the efficacy of improving the health and appearance of a subject can be achieved by administrating an effective amount of Bdph to the subject. Specifically, the Bdph has the efficacy of preventing or treating neurodegenerative diseases such as Alzheimer's disease caused by excessive build up of Aβ in the cells, and as an active ingredient in a topical composition, the Bdph is effective in promoting the hair growth at the site where the Bdph is administered. Furthermore, the method for preparing a pharmaceutical composition containing Bdph disclosed in the present invention comprises preparing the pharmaceutical composition through an organic synthesis reaction, where the Bdph is coated with a polymeric material such as F127 by covalent bonding of the polymeric material with the Bdph, thereby achieving the effect of reducing the cytotoxicity of the pharmaceutical composition for an organism.

Unless otherwise defined herein, the technical and scientific terms used in the specification and claims have the same meanings as those generally understood by persons of ordinary skill in the art to which the invention pertains. In case of contradiction, the present invention shall prevail.

The Bdph disclosed in the present invention has a structural formula as shown in Formula (I):

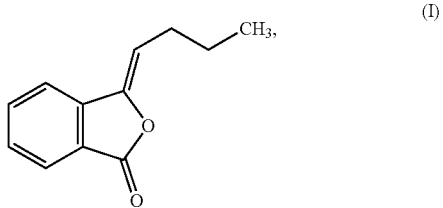 [SMILES: CCC/C=C1\OC(=O)c2ccccc21]

(I)

and is prepared or obtained through a process that is within the general knowledge of those skilled in the art. Such a process is not characteristic of the present invention, and thus is not described in detail herein. For example, Chinese Patent Application No. 200910066666 discloses that Bdph is obtained by extracting plants of the Apiaceae and Asteraceae family with an organic solvent; and Chinese Patent Publication No. 1041725C discloses that Bdph is obtained through chemical synthesis.

The term "hair" as used herein encompasses hairs everywhere on a subject, including, but not limited to, hair, body hair, eyelashes, and eyebrows.

The term "extraction" as used herein refers to a process of transferring a specific component in a mixture from a phase A to a phase B by utilizing the difference in solubility of the material in different extractants, for the purpose of separation, for example, solvent extraction and supercritical fluid extraction. Generally, the extractant comprises, but is not limited to, acetone, chloroform, and carbon dioxide.

The term "chemical synthesis technology" as used herein refers to a series of chemical reactions conducted for obtaining a specific product, such as an organic reaction and an inorganic reaction.

The term "effective amount" as used herein refers to an amount of the desired compound or active ingredient intended for producing a particular effect, and expressed in percentages by weight present in the composition. As will be appreciated by those of ordinary skill in the art to which this invention pertains, the effective amount will vary depending upon the route of administration intended for producing the particular effect. Generally, the active ingredient or compound may be present in the composition in an amount from about 1% to about 100% by weight of the composition, and preferably from about 30% to about 100% by weight of the composition.

The term "pharmaceutically or cosmetically acceptable carrier" as used herein encompasses any standard carrier used in pharmaceutical or cosmetic products, which may be in a solid, semi-solid or liquid form, depending on the type of the compositions. For example, the carriers comprise, but are not limited to, gelatin, an emulsifier, a hydrocarbon mixture, water, glycerin, saline, buffered saline, lanolin, paraffin, beeswax, dimethylsilicone, and ethanol The term "analog" as used herein encompasses salts, esters, and structural isomers such as Z-type or E-type structures of a compound, or products obtained after the structure is modified.

The polymer F127 disclosed in the present invention is a triblock copolymer of polyoxyethylene-polyoxypropylene-polyoxyethylene having a structural formula as shown in Formula (II):

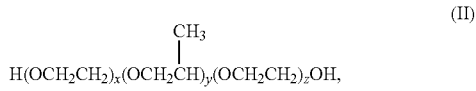

(II)

where x, y, and z are respectively an integer greater than 1. Because the polyoxyethylene at both ends of the polymer F127 is hydrophilic and the middle block of polyoxypropylene is hydrophobic, the polymer F127 is an amphoteric material. When the polymer F127 is present in the aqueous solution, it diffuses gradually to the interface and is adsorbed on the interface, so that the surface tension is decreased. Furthermore, by controlling the proportion of the hydrophobic groups in the polymeric material, the surface activity of the polymeric material is controlled.

The "intermolecular attraction" as used herein includes, but is not limited to, van der Waals force, Coulomb force, hydrogen bonding, and hydrophobic bonding force.

The term "pharmaceutical composition" as used herein comprises an effective amount of a desired compound or active ingredient intended for producing a particular effect, and at least a pharmaceutically acceptable carrier. It can be appreciated by those ordinarily skilled in the art to which the present invention pertains that the form of the pharmaceutical composition varies with the route of administration intended for producing the particular effect, including, for example, tablets, powders and injections; and the carrier can be in a solid state, a semi-solid state or a liquid state, depending on the form of the pharmaceutical composition. For example, the carrier includes, but is not limited to, gelatin, an emulsifier, a hydrocarbon mixture, water, glycerin, saline, buffered saline, lanolin, paraffin, beeswax, dimethylsilicone, and ethanol.

The term "polymeric material" as used herein refers to a macromolecule having a quite high molecular weight which is produced through polymerization. Generally, the polymeric material is an organic molecule.

Hereinafter, for the purpose of further explaining the efficacy of the present invention, the present invention is described in detail by way of examples. However, the examples are illustrative and any language used therein is not intended to limit the specification and the scope and meaning of the claims of the present invention.

It should be noted that n-butylidenephthalide (Bdph, W333301) used in the following examples is obtained from Sigma-Aldrich.

Example 1: Test of Wnt Activity

The baby hamster kidney fibroblast cells BHK21 were prepared in a 6-well culture dish to about 50% confluent. For each well of the culture dish, 50 µl of Opti-MEM medium (Invitrogen) and 2 µl of Lipofectamine 2000 (Invitrogen) were mixed in a 1.5 ml microcentrifuge tube for 5 minutes to form a Lipofectamine mixture.

50 µl of Opti-MEM medium was mixed with 9.6 µg of Top-flash plasmid DNA or Fop-flash plasmid DNA, to form a Top-flash plasmid mixture and a Fop-flash plasmid mixture, where the Top-flash plasmid had a wild-type TCF binding site, and used in a test group; and the Fop-flash plasmid had a mutant TCF binding site, and used in a control group; and the two plasmids were both ligated with a luciferase sequence.

In a first set of tests, the Top-flash plasmid mixture was added to the Lipofectamine mixture, to give a mixture of 100 µl in total. There were 3 groups of mixtures in total. Each group of mixture was stood and reacted at room temperature for 20 min, then transferred to the culture dish, and gently shaken till it was uniformly distributed. Subsequently, the Opti-MEM medium was replenished till the liquid level just covered the cells BHK21, and incubated at 37° C. for 4 hrs. Then the Opti-MEM medium was further replenished till each well contained 2 ml of the medium, and refreshed about every 18-24 hrs. Each group was incubated under different conditions, where the group 1 was a blank group, 0.4 µM compound BIO was added to the group 2, and 0.4 µM Bdph was added to the group 3. Each group was additionally incubated for about 18-24 hrs. Then the cells BHK21 of each group were collected from the culture dish, and detected for the luciferase activity. The result is shown in FIG. 1, in which the symbol * indicates a significance level of 0.05.

In a second set of tests, the Top-flash plasmid mixture or the Fop-flash plasmid mixture was added to the Lipofectamine mixture, to give a Top-flash mixture or Fop-flash mixture of 100 µl in total. There were 4 groups of mixtures in total, where the group 1 was the Fop-flash mixture, and the groups 2 to 4 were the Top-flash mixture. Each group of mixture was stood and reacted at room temperature for 20 min, then transferred to the culture dish, and gently shaken till it was uniformly distributed. Subsequently, the Opti-MEM medium was replenished till the liquid level just covered the cells BHK21, and incubated at 37° C. for 4 hrs. Then the Opti-MEM medium was further replenished till each well contained 2 ml of the medium, and refreshed about every 18-24 hrs. Each group was incubated under different conditions, where 4 µM Bdph was added to the group 1, no compound was added to the group 2, 1 µM Bdph was added to the group 3, and 4 µM Bdph was added to the group 4. Each group was additionally incubated for about 18-24 hrs. Then the cells BHK21 of each group were collected from the culture dish, and detected for the luciferase activity. The result is shown in FIG. 2, in which the symbol * indicates a significance level of 0.05.

The luciferase activity was detected as follows. The medium was aspirated off from the cells BHK21, and then the cells were washed twice with a phosphate buffer. 200 µl of 1×PLB (Passive Lysis Buffer, Promega) was added to each well of the culture dish, and shaken for 15 min at room temperature. After the cells were lysed, the lysate was removed and centrifuged for 1 min at 12000 rpm and 4° C. The supernatant was collected. 20 µl of the supernatant was transferred to a 96-well plate, and 100 µl of a luciferase assay reagent was added and placed in a luminescence meter, for detecting the luciferase activity at a wavelength of 595 nm.

As shown from the result in FIG. 1, the luminescence intensity of the group 1 receiving no treatment with a compound is used as a reference in the test. Compared with the group 1, the luminescence intensity from the cells transfected with Top-flash plasmid DNA is significantly increased when the cells are treated with 0.4 µM compound BIO or Bdph (the groups 2 and 3), indicating that the TCF promoter in the cell is activated, such that the luciferase activity and expression in the cells are detected.

Figure 2:
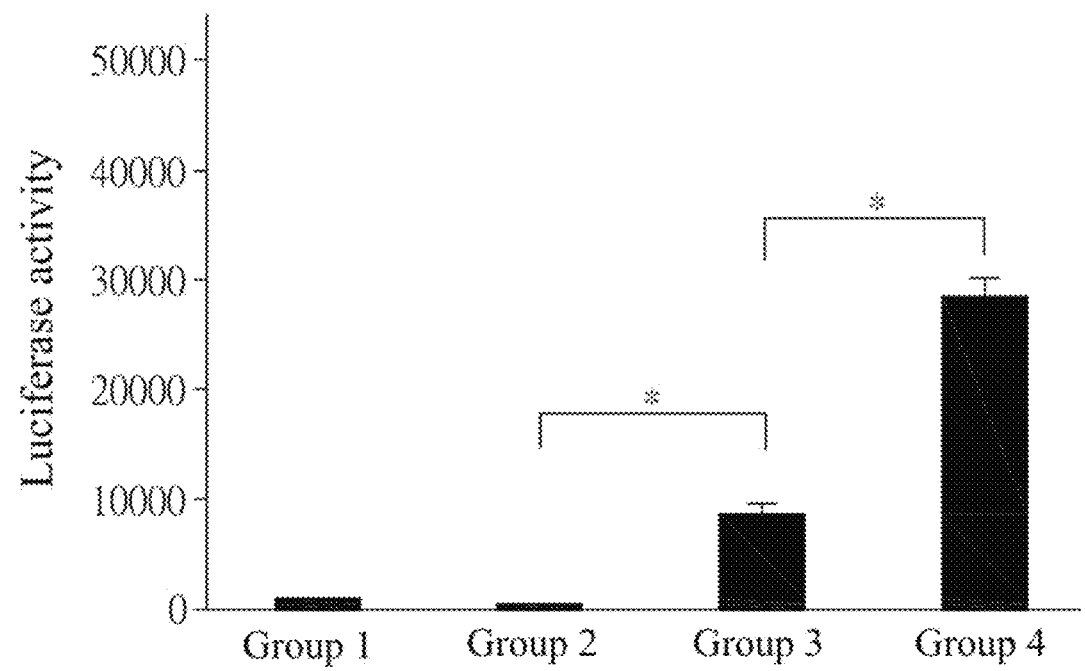
FIG. 2 shows statistical analysis results for luciferase expression detected in each group of cells after the groups of cells transfected with Top-flash plasmid DNA or Fop-flash plasmid DNA are cultured under various conditions.

The result in FIG. 2 shows that since the cells in the group 1 has mutant Fop-Flash reporter, the luciferase activity cannot be detected in the group 1 even though the Bdph is added. In other words, the luminescence intensity from the cells is not increased at all. The luminescence intensity from the cells in the groups 2 to 4 is increased with increasing dosage of Bdph. It can be known that the luciferase activation is specific and dosage dependent.

As pointed out in previous literatures, BIO is a Wnt activating agent that binds to the TCF binding site in the Top-flash plastid and facilitates the luciferase expression when the Wnt signaling is activated in the cell. It can be known from the results of FIGS. 1 and 2 that the Bdph can significantly improve the luciferase activity as the dosage is increased, whereby the Bdph disclosed in the present invention has the ability to activate the Wnt signaling.

Example 2: Animal Test

C57BL/6 male mice aged 6 to 8 weeks were assigned to three groups, each group having two mice. The mice had a hairless region of 2 square centimeters on the epidermis of the back close to the tail. The hairless region was treated daily under various conditions. After 21 days, the hair growth, body weight and appearance of the mice in each group were observed. The group 1 was a control group, in which the hairless region was applied excessively with phosphate buffered saline. The group 2 was a test group, in which the hairless region was applied with an emulsified composition containing 10 μM Bdph. The group 3 was a test group, in which the hairless region was applied with an emulsified composition containing 100 μM Bdph. The results are shown in FIG. 3.

Figure 3:
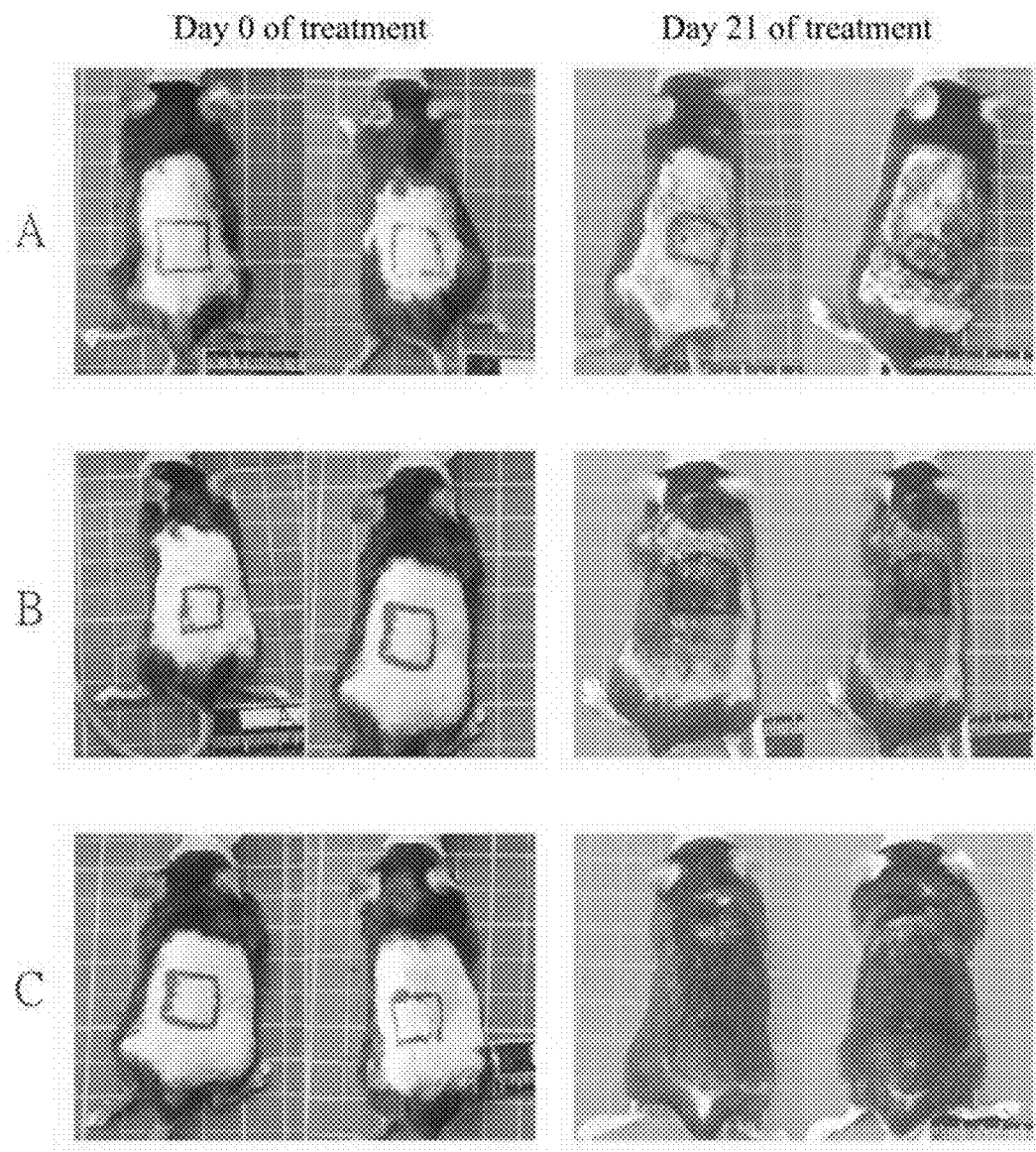
FIG. 3 shows change in appearance of the mice in each group after various treatments.

The results in FIG. 3 show that the body weight of the mice in each group is normal. Compared with the group 1, the hair growth in the hairless region on the back of the mice in the groups 2 and 3 is obvious, and the hair growth in the hairless region on the back of the mice in the group 3 is much significant. It can be known that application of the Bdph disclosed in the present invention can effectively promote the hair growth, and the hair growth promoting effect is obviously increased with increasing dosage.

Example 4: Synthesis of Bdph in Aqueous Phase n-Butylidenephthalide (Bdph, W333301, Sigma-Aldrich) and the F127 polymer (Pluronic F127, P2443) were obtained. 10 mg of Bdph was mixed with the F127 polymer at a weight ratio of 1:1 or 1:2, then dissolved in 2 ml of tetrahydrofuran, and added to 10 ml of water. Afterwards, tetrahydrofuran was removed by rapid heating. The residue was freeze dried, and then dissolved in water again. After being emulsified into the solution, the Bdph had a particle size of about 30-200 nm and a polydispersity index of 0.2-0.5.

Example 5: Cell Culture

The human pluripotent stem cells were incubated in a serum free medium Essential 8™ (Life Technologies, US), and amenable to attachment culture with Matrigel™ matrix (Becton-Dickinson, US). The medium was aspirated off, and then the cells were washed twice with a phosphate buffer. The Accutase™ (Merck Millipore, US) was added, reacted for 2-5 min, and then neutralized with the culture medium. The cells were flushed off, broken up into a small mass, and centrifuged for 2 min at 1000 rpm. The supernatant was aspirated off, and the cells were incubated for 3 to 5 days in a new dish for sub-culture, during which the medium was refreshed every day.

Example 6: Differentiation into Nerve Cells

The human pluripotent stem cells were cultured to 80-90% confluent, washed twice with a phosphate buffer, and treated with the Accutase™ for 2-5 min. The enzyme was diluted with the culture medium. Then the cells were flushed off, broken up into appropriate size, and centrifuged for about 2 min at 800 rpm. The cells were transferred to the DMEM-F12 medium containing 20% knock out serum replacement (KSR, Life Technology, US), and cultured for 2 days in suspension in an open dish, to obtain an embryonic body suspension.

The suspended embryonic body was transferred to a centrifuge tube, and naturally settled down. The supernatant was removed, and the cells were cultured for 2 days in suspension in a neural induction medium containing the BiSF small-molecule drug. Then, the suspended embryonic body assumed an annular structure of epithelial cells. The small-molecule drug contained 0.5 μM BIO (Sigma-Aldrich, US), 10 ng/ml Fibroblast Growth Factor 2 (FGF-2, Peprotech, US), and 10 μM SB431542 (Sigma-Aldrich, US). The ingredients of the neural induction medium are shown in Table 1 below.

TABLE 1

Ingredients of the neural induction medium

| Ingredient | Content (ml) |
| --- | --- |
| DMEM medium (Life technologies, 11965-092) | 326 |
| F12 medium (Life technologies, 11765-054) | 163 |
| N2 supplement (Life technologies, 17502-048) | 5 |
| Non-essential amino acid (Life technologies, 11140-035) | 5 |
| Heparin (1 mg/ml) | 1 |

The embryonic body was settled down, and cultured in a neurobasal medium containing 10 ng/ml FGF-2. The ingredients of the neurobasal medium are shown in Table 2 below. After 2-day culture in suspension, the embryonic body was settled down, broken up into a small mass by an external force or with the Accutase™, transferred to a culture dish having 1% Matrigel™ matrix coated for over 1 hr, and amenable to cell attachment. The cell attachment occurred in about 2 to 7 days, and the nerve structure was grown. The cells were sub-cultured when grown to 70-80% confluent. The sub-culture was as follows. The cells were washed once with a phosphate buffer, treated for about 2-5 min with an enzyme solution of a phosphate buffer and the Accutase™ (1:1), then diluted with a neurobasal medium, scraped off by a cell scraper, and mechanically broken up into a small mass or single cells. The cells were centrifuged for about 2 to 5 min at 800-1000 rpm, and the supernatant was aspirated off. The cells were attached for 1 day, during which 10 μM Y27632 (Stemgent, US) was added to facilitate the cell attachment.

TABLE 2

Ingredients of the neurobasal medium

| Ingredient | Content (ml) |
| --- | --- |
| Neurobasal medium (Life technologies, 21103-049) | 500 |
| N2 supplement (Life technologies, 17502-048) | 5 |
| Non-essential amino acid (Life technologies, 11140-035) | 5 |
| Heparin (1 mg/ml) | 1 |
| B27 supplement (non-essential) (Life technologies, 17504-044) | 10 |

Example 7: Cytotoxicity Test

Figure 4:
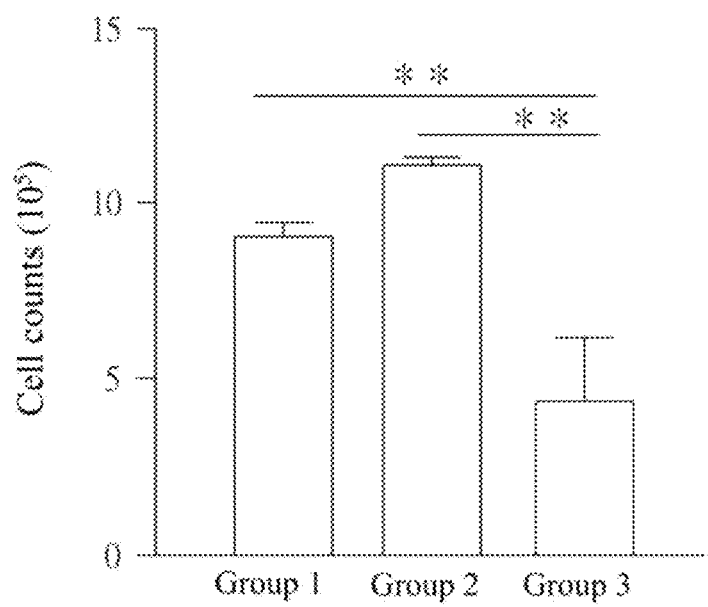
FIG. 4 shows results of cytotoxicity tests using Bdph coated with/without the polymeric material F127.

The human embryonic stem cells TW1 were cultured in the Essential 8™ medium, and divided into three groups upon sub-culture. The cells were inoculated in a 6-well plate at a density of $1.2 \times 10^5$ cells/well, and cultured under the following conditions. The group 1 was cultured with the medium alone; in the group 2, 10 μM Bdph uncoated with the F127 polymer was added to the medium; and in the group 3, 10 μM Bdph coated with the F127 polymer as prepared in Example 1 was added to the medium. The cell morphology in each group was observed during culture, and the cells were counted after 4-5 days of culture. 1-3 measurements were conducted for each group. The results are shown in FIG. 4. The results shown in FIG. 4 are obtained from one-way ANOVA analysis and Tukey's Multiple Comparison Test (P<0.05, 95% confidence level). The symbol * indicates a significance level of 0.05, and the symbol ** indicates a significance level of 0.01.

It can be known from the results in FIG. 4 that after 5-day culture, the cell counts in the group 2 are obviously less than those in the group 1 or 3. Therefore, Bdph has a high cytotoxicity on the cells, and the cytotoxicity of Bdph can be effectively reduced by coating it with the polymer F127.

Example 8: Neural Differentiation Culture of T21-iPSCs

Figure 5:
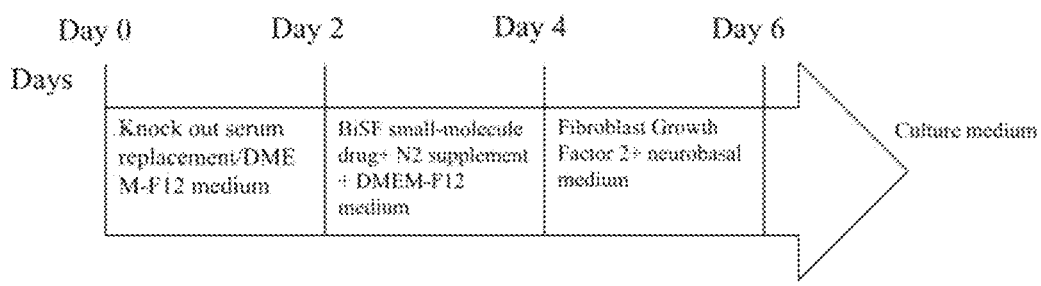
FIG. 5 is a flow chart for neural differentiation culture of T21-iPSCs.
Figure 6:
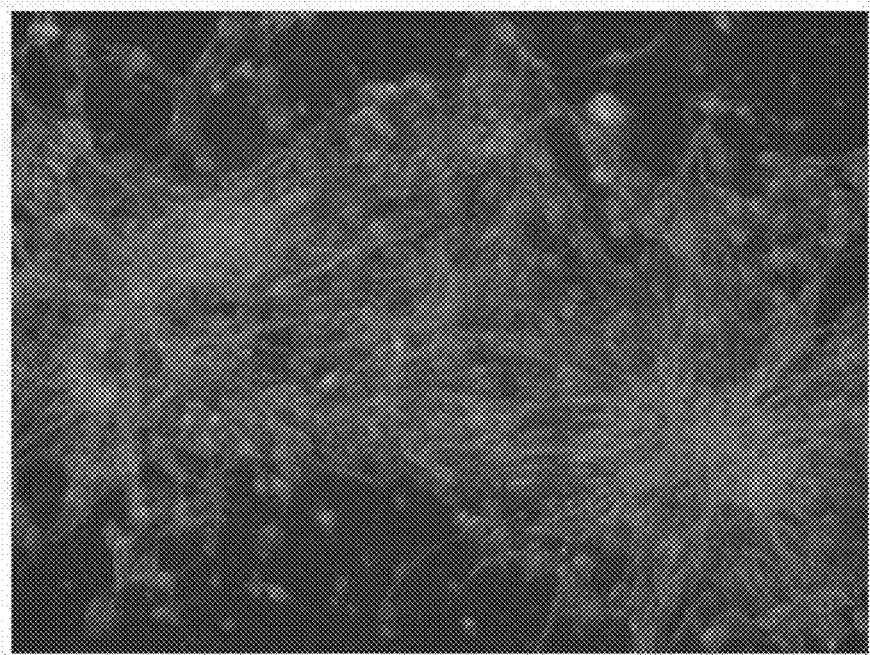
FIG. 6 shows results of N-cadherin expression in T21-iPSCs observed by immunofluorescent staining after the T21-iPSCs are subjected to neural differentiation culture, in which the red indicates the immunofluorescent stained N-cadherin, and the blue indicates the nuclei stained with DAPI.
Figure 7:
FIG. 7 shows results of nestin expression in T21-iPSCs observed by immunofluorescent staining after the T21-iPSCs are subjected to neural differentiation culture, in which the green indicates the immunofluorescent stained nestin, and the blue indicates the nuclei stained with DAPI.
Figure 8:
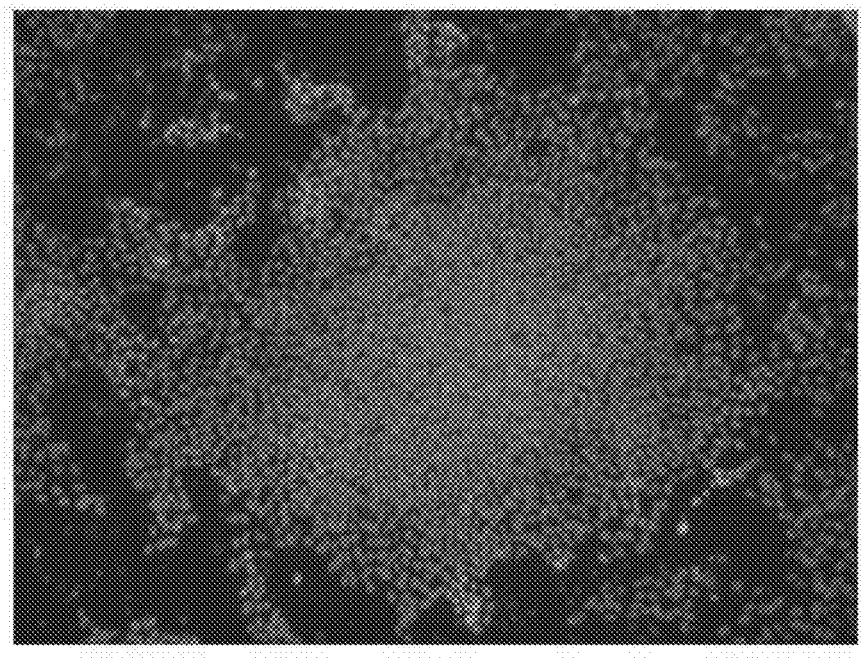
FIG. 8 shows results of Pax-6 protein expression in T21-iPSCs observed by immunofluorescent staining after the T21-iPSCs are subjected to neural differentiation culture, in which the red indicates the immunofluorescent stained Pax-6 protein, and the blue indicates the nuclei stained with DAPI.
Figure 9:
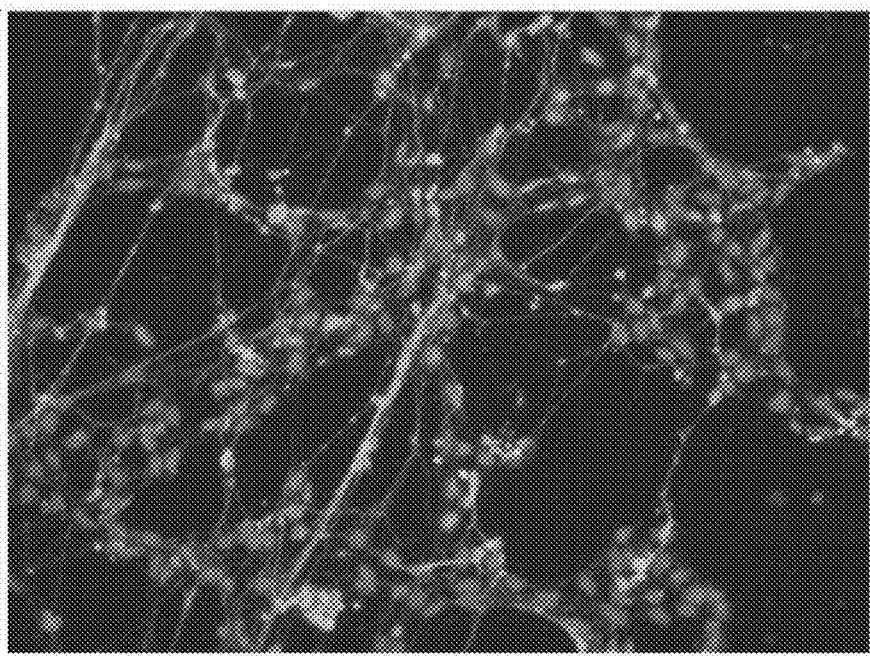
FIG. 9 shows results of βIII tubulin expression and neurite growth in T21-iPSCs observed by immunofluorescent staining after the T21-iPSCs are subjected to neural differentiation culture, in which the green indicates the immunofluorescent stained βIII tubulin, and the blue indicates the nuclei stained with DAPI.

Referring to Example 5 and FIG. 5, neural differentiation of T21-iPSCs was carried out as described in Example 6, and the cells were attached at day 8. The cells was assayed by immunofluorescence staining at day 12 after cell attachment, to observe the expression of markers for neural stem cells, including N-cadherin, Nestin, and Pax-6 protein. The results are shown in FIGS. 6 to 8. The neurite growth was additionally observed after the neural differentiation culture of T21-iPSCs. The cells was assayed by immunofluorescence staining at day 27 of culture, and the expression of mature neuronal markers such as βIII tubulin in the cells was observed with the aid of the antibody Tuj-1. The result is shown in FIG. 9.

The operational process for the assay by immunofluorescence staining was as follows. The cells were cultured in a 4-well culture dish with a cover slip. During staining, the medium was aspirated off from the cells, and then the cells were washed twice with a phosphate buffer. 4% paraformaldehyde (PFA) was added for fixing the cells for 5 min on ice, and then removed. Subsequently, the cells were washed three times with a phosphate buffer, perforated by treating for 10 min with 0.3% triton (PBST) on ice, further washed three times with a phosphate buffer, and blocked for 1 hr with 5% equine serum. The liquid was aspirated off and a primary antibody formulated in 3% equine serum was added. After 4 hr treatment at room temperature or 16 hr reaction at 4° C., the primary antibody was aspirated off, and the cells were washed three times with PBST for 5 min each. The secondary antibody was formulated in a phosphate buffer. The PBST was aspirated off, and then the secondary antibody was added. After 1 hr treatment in the dark, the cells were washed three times with PBST. 1 μg/ml nuclear staining agent DAPI was added, and the cells were treated for 10 min in the dark at room temperature. The cells were washed twice with PBST, impregnated with 200 μl of a mixed solution of glycerin and a phosphate buffer (1:1), picked, mounted, and observed for the fluorescence under an upright fluorescent microscope.

As can be known from the results in FIGS. 6 to 8, T21-iPSCs express proteins specific for neural stem cells, including N-cadherin, Nestin and Pax-6 at day 12 of neural differentiation culture, indicating that T21-iPSCs can be successfully differentiated into T21 nerve cells after culture with the medium above. Moreover, it can be known from the result in FIG. 9 that after 27-day differentiation culture, T21-iPSCs have a large number of neurites, and can express βIII tubulin that is a mature neuronal marker, suggesting that T21-iPSCs are differentiated into mature T21 nerve cells after 27-day differentiation culture.

Example 9: Aβ40 Expression Level in Nerve Cells

The nerve cells differentiated from T21-iPSCs after attachment culture were counted, and attached to a 4-well culture dish. The culture medium was refreshed every 48 hours and the culture medium collected every 48 hours was stored at −20° C. The Aβ40 expression level was analyzed by Enzyme Linked Immunosorbent Assay (ELISA). The nerve cells differentiated from human embryonic stem cells TW1 with normal karyotype were used as the control. Each test was duplicated or triplicated. The analysis results are shown in FIG. 10.

The operational process of the ELISA assay was as follows. The Aβ standard protein in an ELISA kit was serially diluted with a working incubation buffer, for plotting a standard curve. The collected cell culture was 1:2 diluted with the working incubation buffer. 100 μl of the standard solution and the sample were transferred to a 96-well plate and stood at 4° C. for 16 hrs. The liquid was aspirated off, the plate was washed with 300 μl wash buffer and then air dried. 200 μl of TMB substrate was added, the reaction was continued for about 40-45 min in the dark at room temperature, and the absorbance at 620 nm was read.

Figure 10:
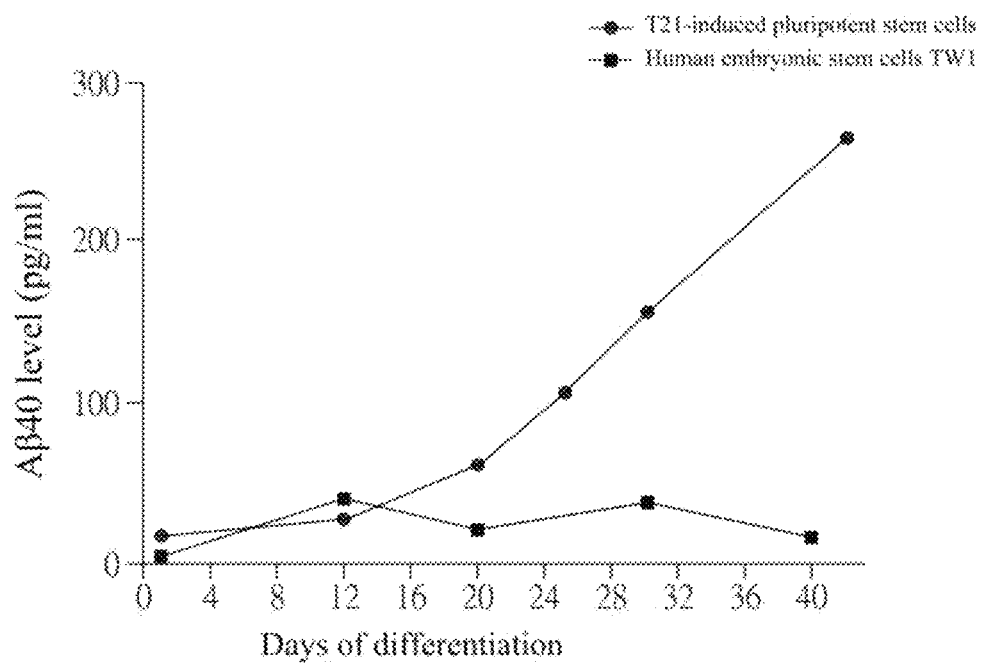
FIG. 10 shows results of Aβ40 expression level in nerve cells differentiated from various cells, as statistically analyzed by Enzyme Linked Immunosorbent Assay (ELISA).

As can be known from the results in FIG. 10, the Aβ40 expression level in the nerve cells differentiated from T21-iPSCs is higher than that in the nerve cells differentiated from human embryonic stem cells TW1 from day 20 of differentiation, and there is difference from day 25 of differentiation. In particular, the Aβ40 expression level in the nerve cells differentiated from T21-iPSCs was 105.38 pg/ml at day 25 of differentiation, 155.68 pg/ml at day 30 of differentiation, and 264.47 pg/ml at day 42 of differentiation.

Accordingly, the Aβ40 expression level in the nerve cells differentiated from T21-iPSCs increases significantly with relapse of the differentiation time and thus can be served as a platform for screening drugs for treating or preventing neurodegenerative diseases.

Example 10: Drug Screening

Figure 11:
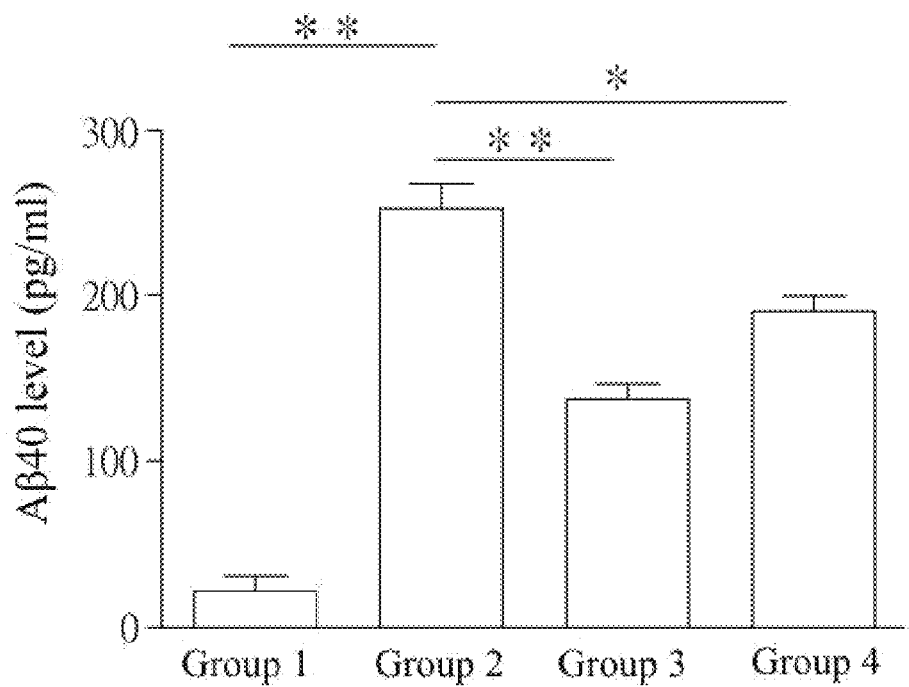
FIG. 11 shows results of Aβ40 expression level in nerve cells differentiated from T21-iPSCs after culture under various treatment conditions, as statistically analyzed by ELIA.

The T21-iPSCs was subjected to neural differentiation culture, divided into three groups at day 39, and cultured for additional 3 days under various culture conditions. At day 42, the Aβ40 level in each group was analyzed by ELISA, and compared with that in T21-iPSCs experiencing no neural differentiation culture. The result is shown in FIG. 11. The group 1 was T21-iPSCs experiencing no neural differentiation culture; and the groups 2 to 4 were T21-iPSCs experiencing neural differentiation culture. In the group 2, no agent was added during culture; in the group 3, the γ-secretase inhibitor DAPT was added at day 39 of culture; and in the group 4, 10 μM Bdph coated with the F127 polymer was added at day 39 of culture. Each test was duplicated or triplicated. One-way ANOVA analysis and Tukey's Multiple Comparison Test were performed to determine whether there is significant difference between the values (P<0.05, 95% confidence level). The symbol * indicates a significance level of 0.05, and the symbol ** indicates a significance level of 0.01.

It can be known from the results in FIG. 11 that the Aβ40 level in the group 1 is significantly lower than that in the group 2, and the Aβ40 level in the groups 3 and 4 was lower than that of the group 2. Therefore, the Bdph disclosed in the present invention can significantly reduce the Aβ40 level in the nerve cells, and the effect is comparable to that found when the γ-secretase inhibitor DAPT is administered. Thus, the Bdph disclosed in the present invention really has the capability of ameliorating or alleviating the excessive build up of Aβ in the cells, thereby achieving the efficacy of treating or preventing neurodegenerative diseases.

It can be known from the results obtained in the experimental examples that the Bdph disclosed in the present invention has the ability to activate the Wnt signaling, and thus the efficacy of promoting the hair growth. Therefore, the Bdph or an analog thereof disclosed in the present invention can act as an active ingredient in a topical composition for promoting the hair growth and is administered to the skin of a particular site of a subject by spraying, applying, and other routes, for the purpose of promoting the hair growth and improving the appearance of the subject, while the adverse effects of conventional products to the subject are avoided. In addition, in the method for preparing the pharmaceutical composition disclosed in the present invention, a polymeric material is used as a drug carrier to alleviate or reduce the cytotoxicity of Bdph, which can really effectively enhance the safety of the pharmaceutical composition. The pharmaceutical composition produced by the above method does have a function of decreasing the Aβ level in the cells. Therefore, it is possible to achieve the efficacy of treating or preventing neurodegenerative diseases by administering an effective amount of the pharmaceutical composition to an organism.

While the present invention has been described in detail by way of examples, it should be understood that various changes or modifications may be made to embodiments in the specification by those skilled in the art without departing from the spirit of the present invention, which are all contemplated in the protection scope as defined by the claims of the present invention.

REFERENCE

Messenger, A. G. and J. Rundegren, Minoxidil: mechanisms of action on hair growth. Br J Dermatol, 2004. 150(2): p. 186-94.

Woodward, D. F., J. W. Wang, and N. J. Poloso, Recent progress in prostaglandin F2alpha ethanolamide (prostamide F2alpha) research and therapeutics. Pharmacol Rev, 2013. 65(4): p. 1135-47.

Ko, W. C., A newly isolated antispasmodic—butylidenephthalide. Jpn J Pharmacol, 1980. 30(1): p. 85-91.

Teng, C. M., et al., Antiplatelet effect of butylidenephthalide. Biochim Biophys Acta, 1987. 924(3): p. 375-82.

Huang, M. H., et al., Brain tumor senescence might be mediated by downregulation of S-phase kinase-associated protein 2 via butylidenephthalide leading to decreased cell viability. Tumour Biol, 2014.

Tsai, N. M., et al., The natural compound n-butylidenephthalide derived from *Angelica sinensis* inhibits malignant brain tumor growth in vitro and in vivo. J Neurochem, 2006. 99(4): p. 1251-62.

Fu, R. H., et al., Lipopolysaccharide-stimulated activation of murine DC2.4 cells is attenuated by n-butylidenephthalide through suppression of the NF-kappaB pathway. Biotechnol Lett, 2011. 33(5): p. 903-10.

Liu, S. P., et al., n-Butylidenephthalide (BP) maintains stem cell pluripotency by activating Jak2/Stat3 pathway and increases the efficiency of iPS cells generation. PLoS One, 2012. 7(9): p. e44024.

Fodde, R. and T. Brabletz, Wnt/beta-catenin signaling in cancer stemness and malignant behavior. Curr Opin Cell Biol, 2007. 19(2): p. 150-8.

Lim, X. and R. Nusse, Wnt signaling in skin development, homeostasis, and disease. Cold Spring Harb Perspect Biol, 2013. 5(2).

Thompson, C. C., J. M. Sisk, and G. M. Beaudoin, 3rd, Hairless and Wnt signaling: allies in epithelial stem cell differentiation. Cell Cycle, 2006. 5(17): p. 1913-7.

Gat, U., et al., De Novo hair follicle morphogenesis and hair tumors in mice expressing a truncated beta-catenin in skin. Cell, 1998. 95(5): p. 605-14. Ito, M., et al., Wnt-dependent de novo hair follicle regeneration in adult mouse skin after wounding. Nature, 2007. 447(7142): p. 316-20.

Beyreuther, K., T. Dyrks, C. Hilbich, U. Monning, G. Konig, G. Multhaup, P. Pollwein and C. L. Masters (1992). "Amyloid precursor protein (APP) and beta A4 amyloid in Alzheimer's disease and Down syndrome." Prog Clin Biol Res 379: 159-182.

Birks, J. (2006). "Cholinesterase inhibitors for Alzheimer's disease." Cochrane Database Syst Rev(1): CD005593.

Burger, P. C. and F. S. Vogel (1973). "The development of the pathologic changes of Alzheimer's disease and senile dementia in patients with Down's syndrome." Am J Pathol 73(2): 457-476.

Farlow, M. R., G. Alva, X. Meng and J. T. Olin (2010). "A 25-week, open-label trial investigating rivastigmine transdermal patches with concomitant memantine in mild-to-moderate Alzheimer's disease: a post hoc analysis." Curr Med Res Opin 26(2): 263-269.

Feldman, H. H., F. A. Schmitt, J. T. Olin and M. E. M. M. D. S. G. Memantine (2006). "Activities of daily living in moderate-to-severe Alzheimer disease: an analysis of the treatment effects of memantine in patients receiving stable donepezil treatment." Alzheimer Dis Assoc Disord 20(4): 263-268.

Glenner, G. G. and C. W. Wong (1984). "Alzheimer's disease: initial report of the purification and characterization of a novel cerebrovascular amyloid protein." Biochem Biophys Res Commun 120(3): 885-890.

Goedert, M., C. M. Wischik, R. A. Crowther, J. E. Walker and A. Klug (1988). "Cloning and sequencing of the cDNA encoding a core protein of the paired helical filament of Alzheimer disease: identification as the microtubule-associated protein tau." Proc Natl Acad Sci USA 85(11): 4051-4055.

Grundke-lqbal, I., K. Iqbal, Y. C. Tung, M. Quinlan, H. M. Wisniewski and L. I. Binder (1986). "Abnormal phosphorylation of the microtubule-associated protein tau (tau) in Alzheimer cytoskeletal pathology." Proc Natl Acad Sci USA 83(13): 4913-4917.

Gyure, K. A., R. Durham, W. F. Stewart, J. E. Smialek and J. C. Troncoso (2001). "Intraneuronal abeta-amyloid precedes development of amyloid plaques in Down syndrome." Arch Pathol Lab Med 125(4): 489-492.

Hong-Qi, Y., S. Zhi-Kun and C. Sheng-Di (2012). "Current advances in the treatment of Alzheimer's disease: focused on considerations targeting Abeta and tau." Transl Neurodegener 1(1): 21.

Howard, R., R. McShane, J. Lindesay, C. Ritchie, A. Baldwin, R. Barber, A. Burns, T. Dening, D. Findlay, C. Holmes, A. Hughes, R. Jacoby, R. Jones, R. Jones, I. McKeith, A. Macharouthu, J. O'Brien, P. Passmore, B. Sheehan, E. Juszczak, C. Katona, R. Hills, M. Knapp, C. Ballard, R. Brown, S. Banerjee, C. Onions, M. Griffin, J. Adams, R. Gray, T. Johnson, P. Bentham and P. Phillips (2012). "Donepezil and memantine for moderate-to-severe Alzheimer's disease." N Engl J Med 366(10): 893-903.

Hussain, I., D. Powell, D. R. Howlett, D. G. Tew, T. D. Meek, C. Chapman, I. S. Gloger, K. E. Murphy, C. D. Southan, D. M. Ryan, T. S. Smith, D. L. Simmons, F. S. Walsh, C. Dingwall and G. Christie (1999). "Identification of a novel aspartic protease (Asp 2) as beta-secretase." Mol Cell Neurosci 14(6): 419-427.

Jarrett, J. T., E. P. Berger and P. T. Lansbury, Jr. (1993). "The carboxy terminus of the beta amyloid protein is critical for the seeding of amyloid formation: implications for the pathogenesis of Alzheimer's disease." Biochemistry 32(18): 4693-4697.

Maidment, I. D., C. G. Fox, M. Boustani, J. Rodriguez, R. C. Brown and C. L. Katona (2008). "Efficacy of memantine on behavioral and psychological symptoms related to dementia: a systematic meta-analysis." Ann Pharmacother 42(1): 32-38.

Masters, C. L., G. Simms, N. A. Weinman, G. Multhaup, B. L. McDonald and K. Beyreuther (1985). "Amyloid plaque core protein in Alzheimer disease and Down syndrome." Proc Natl Acad Sci USA 82(12): 4245-4249.

McShane, R., A. Areosa Sastre and N. Minakaran (2006). "Memantine for dementia." Cochrane Database Syst Rev (2): CD003154.

Mori, C., E. T. Spooner, K. E. Wisniewsk, T. M. Wisniewski, H. Yamaguch, T. C. Saido, D. R. Tolan, D. J. Selkoe and C. A. Lemere (2002). "Intraneuronal Abeta42 accumulation in Down syndrome brain." Amyloid 9(2): 88-102.

Mullard, A. (2012). "Sting of Alzheimer's failures offset by upcoming prevention trials." Nat Rev Drug Discov 11(9): 657-660.

Rumble, B., R. Retallack, C. Hilbich, G. Simms, G. Multhaup, R. Martins, A. Hockey, P. Montgomery, K. Beyreuther and C. L. Masters (1989). "Amyloid A4 protein and its precursor in Down's syndrome and Alzheimer's disease." N Engl J Med 320(22): 1446-1452.

Selkoe, D. J. (1996). "Amyloid beta-protein and the genetics of Alzheimer's disease." J Biol Chem 271(31): 18295-18298.

Shi, Y., P. Kirwan, J. Smith, G. MacLean, S. H. Orkin and F. J. Livesey (2012). "A human stem cell model of early Alzheimer's disease pathology in Down syndrome." Sci Transl Med 4(124): 124ra129.

Siemers, E., M. Skinner, R. A. Dean, C. Gonzales, J. Satterwhite, M. Farlow, D. Ness and P. C. May (2005). "Safety, tolerability, and changes in amyloid beta concentrations after administration of a gamma-secretase inhibitor in volunteers." Clin Neuropharmacol 28(3): 126-132.

Tariot, P. N., M. R. Farlow, G. T. Grossberg, S. M. Graham, S. McDonald, I. Gergel and G. Memantine Study (2004). "Memantine treatment in patients with moderate to severe Alzheimer disease already receiving donepezil: a randomized controlled trial." JAMA 291(3): 317-324.

Tong, G., J. S. Wang, O. Sverdlov, S. P. Huang, R. Slemmon, R. Croop, L. Castaneda, H. Gu, O. Wong, H. Li, R. M. Berman, C. Smith, C. F. Albright and R. C. Dockens (2012). "Multicenter, randomized, double-blind, placebo-controlled, single-ascending dose study of the oral gamma-secretase inhibitor BMS-708163 (Avagacestat): tolerability profile, pharmacokinetic parameters, and pharmacodynamic markers." Clin Ther 34(3): 654-667.

Vassar, R., B. D. Bennett, S. Babu-Khan, S. Kahn, E. A. Mendiaz, P. Denis, D. B. Teplow, S. Ross, P. Amarante, R. Loeloff, Y. Luo, S. Fisher, J. Fuller, S. Edenson, J. Lile, M. A. Jarosinski, A. L. Biere, E. Curran, T. Burgess, J. C. Louis, F. Collins, J. Treanor, G. Rogers and M. Citron (1999). "Beta-secretase cleavage of Alzheimer's amyloid precursor protein by the transmembrane aspartic protease BACE." Science 286(5440): 735-741.

Wolfe, M. S., W. Xia, B. L. Ostaszewski, T. S. Diehl, W. T. Kimberly and D. J. Selkoe (1999). "Two transmembrane aspartates in presenilin-1 required for presenilin endoproteolysis and gamma-secretase activity." Nature 398 (6727): 513-517.

Yiannopoulou, K. G. and S. G. Papageorgiou (2013). "Current and future treatments for Alzheimer's disease." Ther Adv Neurol Disord 6(1): 19-33.

Yu, G., M. Nishimura, S. Arawaka, D. Levitan, L. Zhang, A. Tandon, Y. Q. Song, E. Rogaeva, F. Chen, T. Kawarai, A. Supala, L. Levesque, H. Yu, D. S. Yang, E. Holmes, P. Milman, Y. Liang, D. M. Zhang, D. H. Xu, C. Sato, E. Rogaev, M. Smith, C. Janus, Y. Zhang, R. Aebersold, L. S. Farrer, S. Sorbi, A. Bruni, P. Fraser and P. St George-Hyslop (2000). "Nicastrin modulates presenilin-mediated notch/glp-1 signal transduction and betaAPP processing." Nature 407(6800): 48-54.

What is claimed is:

1. A method for promoting hair growth, comprising administrating a topical composition to the skin of a human in need of such treatment, wherein the topical composition comprises an effective amount of butylidenephthalide (Bdph), and a pharmaceutically or cosmetically acceptable carrier.

2. The method according to claim 1, wherein the skin is a region having hair follicles.

3. The method according to claim 1, wherein the topical composition for promoting hair growth is directly applied onto the skin of the human.

4. The method according to claim 1, wherein the topical composition for promoting hair growth is sprayed onto the skin of the human.

5. The method according to claim 1, wherein a concentration of the compound of butylidenephthalide (Bdph) is from 1 µM to 1 mM.

6. The method according to claim 1, wherein the Bdph is extracted from plants of the Apiaceae family.

7. The method according to claim 1, wherein the Bdph is extracted from plants of the Asteraceae family.

8. The method according to claim 1, wherein the Bdph is capable of activating Wnt signaling.

* * * * *